United States Patent [19]

Fillipova

[11] Patent Number: 5,393,461
[45] Date of Patent: Feb. 28, 1995

[54] PREPARATION OF STABLE AQUEOUS EMULSIONS OF WATER-INSOLUBLE PARTICLES

[75] Inventor: Irina V. Fillipova, Bethlehem, Pa.

[73] Assignee: RTD Corporation, Bethlehem, Pa.

[21] Appl. No.: 131,448

[22] Filed: Oct. 4, 1993

[51] Int. Cl.$^6$ .................. B01J 13/00; C08K 3/04; C08K 3/22
[52] U.S. Cl. .................. 252/314; 106/23 C; 106/472; 252/310; 252/311; 252/312; 252/315.2; 514/937; 514/938; 514/942; 514/952; 523/502; 523/505
[58] Field of Search .............. 252/310, 311, 312, 314, 252/315.2; 514/937, 938, 942, 952; 106/23 C; 523/502, 505

[56] References Cited

U.S. PATENT DOCUMENTS

| | | | |
|---|---|---|---|
| 2,764,499 | 9/1956 | Porter, Jr. | 252/314 X |
| 3,133,893 | 5/1964 | Newman | 524/720 |
| 3,544,500 | 12/1970 | Osmond et al. | 428/402.24 |
| 3,580,880 | 5/1971 | Clarke et al. | 524/457 |
| 4,421,660 | 12/1983 | Solc nee Hajna | 252/62.54 |
| 4,997,864 | 3/1991 | Waters | 523/319 |
| 5,032,390 | 7/1991 | Iwaya et al. | 424/59 |
| 5,066,485 | 11/1991 | Brieva et al. | 424/63 |
| 5,091,188 | 2/1992 | Ahynes | 424/450 |
| 5,171,572 | 12/1992 | Suganuma et al. | 424/401 |
| 5,250,289 | 10/1993 | Boothroyd et al. | 424/59 |

FOREIGN PATENT DOCUMENTS 610397  12/1960  Canada ................. 523/502

*Primary Examiner*—Richard D. Lovering

[57] ABSTRACT

A process for preparing an emulsion of water-insoluble particles useful in the cosmetic, pharmaceutical, paint and ink industries comprising:
  treating the water-insoluble particles with a wetting agent in an organic solvent;
  combining the water-insoluble particles with an oily or polymeric substance to obtain an oily suspension;
  preparing an aqueous solution of a combination of surface active agents; and
  combining the aqueous solution with the oily suspension to form an emulsion.

7 Claims, No Drawings

/ 1

PREPARATION OF STABLE AQUEOUS EMULSIONS OF WATER-INSOLUBLE PARTICLES

BACKGROUND OF THE INVENTION

1. Field of the Invention

This invention relates to stable aqueous emulsions of water-insoluble particles useful in the cosmetic, pharmaceutical, paint and ink industries.

2. Reported Developments

The prior art has expended great effort to provide stable emulsions of particulates for various applications in the above-mentioned industries. The main problem encountered with emulsions is inadequate physical stability whereby the particulates flocculate, agglomerate and settle-out from the emulsions and become non-uniform.

U.S. Pat. No. 3,133,893 discloses pigment particles coated with a polymer for coloring of plastics, resins and synthetic fibers. The polymer is a thermoplastic, linear, addition polymer of a compound containing the polymerizable group of

U.S. Pat. No. 3,544,500 discloses a process for encapsulating solid particles for use in insecticides, pharmaceuticals and powders. The process comprises adsorbing a polymer on the surface of the particles and providing a stabilizer having an anchor group which become associated with the adsorbed polymer on the surface and a pendant hydrophilic component solvated by the aqueous phase and provides a stabilizing sheath around the solid particles.

U.S. Pat. No. 3,580,880 discloses a process for making dispersions of particulate solids by dispersing the particulate solids in a lipophilic or a hydrophilic liquid in the presence of a polymeric amphipathic stabilizer which associates with the surface of the particles and provides a solvated steric barrier around the particles.

U.S. Pat. No. 4,421,660 discloses a process for preparing compositions comprising the steps of:
  emulsifying a hydrophilic emulsion polymerizable monomer in an aqueous dispersion of discrete particles of an inorganic solid; and
  polymerizing the monomer to coat the discrete particles of the inorganic solid.

While the above-listed and similar approaches made great strides in satisfying the needs of various industries, they do have some shortcomings including the complexity of the processes and less than the desired stability in the products produced thereby. The present invention intends to provide solutions for these and other shortcomings.

SUMMARY OF THE INVENTION

The present invention provides a process for making an emulsion comprising the steps of:
  a) preparing a solution of from about 0.01 to about 5% w/w of a wetting agent in an organic solvent to obtain a wetting solution;
  b) mixing of 1 to 90% w/w of a finely divided powder having 50 to 100 nm particle size distribution with the wetting solution to obtain a dispersion;
  c) mixing the dispersion with of from about 10 to about 99% w/w of an oily/polymeric substance dissolved in an organic solvent to obtain an oily suspension;
  d) preparing an aqueous solution by mixing in water of from about 0.1 to about 2.0% w/w of an emulsifying agent selected from the group consisting of a cationic, nonionic, anionic and zwitterionic surface active agent by stirring for about 30 to 90 minutes at a temperature of from about 60° to about 70° C. to obtain an aqueous solution;
  e) cooling the aqueous solution to room temperature;
  f) adding from about 20 to about 35% w/w of the oily/polymeric suspension to from about 65 to about 80% w/w of the aqueous solution and mixing them for about 20 to 30 minutes at room temperature to obtain an aqueous suspension;
  g) emulsifying the aqueous suspension by using emulsifying means, such as a sonifier to obtain an emulsion which contains organic solvents used in step (a); and
  h) removing the organic solvent by stirring/evaporation or other means to obtain a final emulsion essentially free of the organic solvent.

The concentration of the final emulsion may be controlled by either varying the percentage of the oily suspension obtained in step (c), added to the aqueous solution obtained in step (d), or by evaporation of the water from the final emulsion obtained in step (h).

DETAILED DESCRIPTION OF THE INVENTION

An important requirement in the preparation of the emulsion of the present invention is the use of narrow distribution size particles, namely of from about 50 or less nm to about 100 nm.

Water-insoluble Particles

The finely-divided particles used in the present invention should be essentially water-insoluble. Such particles may be inorganic, organic and polymeric particles depending on the intended end use of the emulsion. The required particle size is achieved by conventional techniques, such as by grinding, milling or comminution.

Examples of inorganic particles include, but are not limited to zinc oxide, talc, kaolin, mica, titanium dioxide, zirconium oxide, iron oxides, aluminum hydroxide, aluminum chloride, calcium phosphate, magnesium oxide, aluminum silicate, calcium silicate, titanium dioxide, bentonite, asbestine, china clay, calcium carbonate, magnesium carbonate and dolomite.

Examples of organic and polymeric particles include, but are not limited to, starch, polyamide resin, polyolefin resins, polystyrene, polystyrene resin, acrylic resin, epoxy resin, vinyl resin, vinylidene resin, polyurethane resin, natural rubber, synthetic rubber, chitin, chitosan, fibroin, keratin and cellulose.

Some of these materials are extensively used in the various industries for various purposes. For example: zinc oxide is used in dusting powders, pastes, ointments, creams and lotions; talc, titanium dioxide and zinc oxide are used in cosmetic powders; titanium dioxide and zinc oxide are used as sunblockers; antimony oxide, red oxide, lemon chrome, cobalt blue, metal containing organic pigments and carbon blacks are used as pigments in the paint and printing industries.

When materials are ground, milled or comminuted to very small particle size, air is adsorbed onto the surface of the particles. The adsorbed air prevents or at least greatly reduces the wettability of the particles thereby hindering uniform suspensions of the particles in a liquid vehicle. For this reason a wetting agent must be used to replace solid-air interface with a solid liquid interface.

In non-aqueous solutions the molecules of a wetting agent are oriented with the hydrophobic group towards the molecules of the nonaqueous solution thereby increasing the hydrophobicity of the solid particles and rendering them more wettable. The prior art has utilized aqueous, oily, waxy or volatile organic vehicles for dispersing solid particles for obtaining the desired effects in the various end products. While the use of these approaches and materials provided improvements in emulsions, the need for further improvements are obvious for those practicing in the cosmetic, paint, pharmaceutical and printing industries.

Wetting Agents

The wetting agents used in an organic solvent in step (a) of the process to provide a wetting solution include but are not limited to: sodium dodecyl benzene sulfonate, alkyl benzene sulfonate, sodium lauryl sulfate, sodium dioctyl sulfosuccinate, sodium-dilauryl phosphate, lanolin and lanolin derivatives, sodium monoglyceryl lauryl sulfate, sodium methyl oleoyl taurate, sodium octoxynol-2-ethanesulfonate, sodium dioctyl sulfosuccinate, sodium octoxynol-2-ethane sulfonate, di-$\beta$-naphthylmethane disulfate, sulfated castor oil, sodium secondary alcohol sulfate, sodium alkylaryl sulfonate (AEROSOL OS), dialkylsulfosuccinate (AEROSOL MA), dioctyl ester of sodium sulfosuccinate (AEROSOL OT), sodium-2-ethylhexyl sulfate (TERGITOL 08), sodium-7-ethyl-2-methyl-undecyl-4-sulfate (TERGITOL 04), and sodium-3,9-diethyltridecyl-6-sulfate (TERGITOL 07).

Emulsifying Agents

The emulsifying agents used in an aqueous solution in step (d) of the process include, but are not limited to:

Cationic surfactants which include long-chain amino condensates with ethylene oxide and quaternary ammonium compounds, such as cetyl trimethyl ammonium bromide and dodecyl dimethyl ammonium bromide, hexadecyl (cetyl) trimethylammonium bromide, dodecyl pyridinium chloride and dodecylamine hydrochloride.

Anionic surfactants include: salts of aliphatic monoesters of sulfuric acid and soaps, such as sodium lauryl sulphate and sodium heptadecyl sulphate; sulfonated aromatic agents such as alkyl benzene sulfonic acids and salts thereof, such as tridecylbenzene sulphonic acid and the sodium and amino salts of dodecylbenzene sulphonic acid; alkyl naphthalene sulfonates, such as sodium butylnaphthalene sulphonate, sulphosuccinates such as sodium dioctyl sulphosuccinate and N-acyl-N-alkyl fatty acid taurates; sulfated polyoxyethylated alcohols; and sulfated oils.

Non-ionic surfactants which include: polyethylene oxide condensates of alkylphenols, such as octyl cresol, octyl phenol or nonyl phenol with ethylene oxide; ethoxylated aliphatic alcohols which are the condensation products of aliphatic alcohols having from about 8 to 18 carbon atoms, for example, oleyl or cetyl oxide, with ethylene oxide wherein the ethylene oxide is present in equal amounts of from about 30 to 60 moles of ethylene oxide per mole of alcohol; and carboxylic esters formed by the reaction of fatty acids with polyhydric alcohols. Other nonionic surfactants include: polyoxyethylene p-tert-octylphenyl ether and polyoxyethylene monohexadecyl ether.

Zwitterionic surfactants include N-dodecyl-N,N-dimethyl betaine.

Preferred emulsifying agents include: potassium laurate, sodium dodecyl sulfate, ammonium lauryl sulfate, magnesium lauryl sulfate, triethanolamine lauryl sulfate, sulfated castor oil, dialkylglycerylphosphorylcoline, sodium lauryl sulfoacetate, sodium dodecyl benzenesulfonate, polyoxyethylated lauryl, hexadecyltrimethylammonium bromide or chloride, ethoxylated paraoctylphenol, 2-ethyl-hexyl alcohol, ethoxylate and cetyltrimethyl ammonium persulfate.

The surfactants used as emulsifying agents are preferably used with a co-surfactant. The ratio of surfactant to co-surfactant should be in the range of 1:1 to 1:3 for best results.

Co-surfactants include: lauryl-, cetyl-, miristyl-, stearyl, oleyl- and isocetyl-alcohols, lanolin and its derivatives, hexadecane, 1-pentanol, hexanol and decane.

In the process the co-surfactant must be added to the aqueous phase together with the surfactant.

The Oily/Polymeric Substance

The oily substances used in the present invention include, but are not limited to, oils and fats, such as: fatty alcohols, for example, cetyl alcohol, lauryl alcohol and stearyl alcohol; vegetable oils, for example, olive oil, grape seed oil, safflower oil, soybean oil, corn oil, rapeseed oil, avocado oil, almond oil, castor oil, peanut oil, coconut oil, and cottonseed oil; animal fats, for example, tallow, mink oil, and hardened oil; waxes, for example, shellac, beeswax, lanolin, liquid lanolin, carunauba wax and candelilla wax; and hydrocarbons, for example, liquid paraffin and squalane, and petrolatum.

The Organic Solvent

An organic solvent or a mixture of organic solvents is used to dissolve the wetting agent as well as to dissolve the oily/polymeric substance. The type of organic solvent used depends on the solubility of the wetting agent and the oily/polymeric substance. Preferred solvents are those that volatilize easily and do not leave undesirable odor. Examples of solvents include ethyl alcohol, methyl alcohol, isopropyl alcohol, chloromethane, dichloromethane, chloroform, carbon tetrachloride, methyl ethyl ketone, methyl isobutyl, ketone, ethyl acetate, perchloroethylene, acetone and glycol ethers.

Comminution of the Particles

The particles used in the present invention should be in the range of from about 50 to about 100 nm or less. The required particle size powder may be obtained by using methods of particle-size reduction known in the art, such as by grinding, sonification, high pressure and shear and high speed impact in air.

The present invention will now be illustrated by the following examples.

EXAMPLE 1

Paint and Ink Preparations a) 0.01 g of alkylbenzylsulfonate was dissolved in 12 ml of acetone to obtain a wetting solution.
b) 2 g of carbon black was mixed with the wetting solution to obtain a dispersion.
c) The dispersion was mixed with a solution of 2 g of epoxide resin and 2 g of a vinyl polymer in dichloromethane to obtain an oily suspension.
d&e) 0.2 g of sodium lauryl sulfate and 0.6 g of cetyl alcohol were dissolved in deionized water at a temperature of 65° C., followed by cooling to room temperature to obtain an aqueous solution.
f&g) The suspension (c) and aqueous solution (d&e) were then added together and stirred for 15 to 30 minutes at room temperature and emulsified by a sonifier.
h) The organic solvents, acetone and dichloromethane were removed from the emulsion by evaporation using a magnetic stirrer.

EXAMPLE 2

Paint and Ink Preparations a) 0.4 g of alkylaryl sulfonate (AEROSOL OS) was dissolved in 30 ml of carbon tetrachloride to obtain a wetting solution.
b) 18 g of manganese dioxide was mixed with the wetting solution to obtain a dispersion.
c) The dispersion was mixed with a solution of 18 g of chlorinated rubber and 18 g of an acrylic polymer in chloromethane to obtain an oily suspension.
d&e) 0.5 g of sodium dodecyl sulfate and 1.5 g of stearyl alcohol were dissolved in 98 g of deionized water at a temperature of 70° C., followed by cooling to room temperature to obtain an aqueous solution.

The remaining process steps were performed as described in Example 1.

Table I shows typical preparations useful in the paint and ink industries wherein ingredients from the columns are combined according to the process described in Example 1.

TABLE I

| Paint and Ink Preparations | | | | |
|---|---|---|---|---|
| 0.01 to 5% w/w Wetting Agent selected from the group | 2 to 18% w/w of Oily Substance selected from the group | 0.1 to 2.0% w/w of Emulsifying Agent selected from the group | 2 to 18% w/w of Particulate selected from the group | 20–80 ml of Organic Solvent selected from the group |
| Alkyl-benzene-sulfonate, Dioctyl ester sodium sulfosuccinate (AEROSOL OT), Sodium alkylaryl sulfonate (AEROSOL OS), Diethyl sulfosuccinate (AEROSOL MA), Sodium-2-ethylarylsulfate (TERGITOL 08), Sodium-3,9-diethyltridecyl-6-sulfate (TERGITOL 07), Sodium-7-ethyl-2-methyl-undecyl-4-sulfate (TERGITOL 04) Lanolin triethanolamine stearate | Phenolic resin, Epoxide resin, Chlorinated Rubber, Amino Resin, Urethane resin, Urethane oil, Polyurethane unsaturated polyester, Nitrocellulose, Acrylic polymer, Acrylic-copolymer, Vinyl polymer, Vinyl co-polymer, Styrene polymer, Styrene co-polymer | Sodium lauryl sulfate, Sodium dodecyl sulfate, Cetyl alcohol, Stearyl alcohol, Alkane hexadecane | Carbon black, Copper carbonate, Manganese Dioxide, Zinc chromate, Barium chromate, Cadmium sulfide, Iron oxide, Ultramarine, Prussian blue, Cobalt blue, Chromium oxide, Red iron oxide, Titanium dioxide, Zinc oxide, Antimony oxide, Lead carbonate | Chloromethane, Dichloro-methane, Chloroform, Carbon tetra-chloride, Methyl ethyl ketone, Methyl isobutyl ketone, Ethyl acetate, Perchloro-ethylene, Isopropanol, Acetone, Methanol, Ethanol Butanol Propanol Iso-propanol Iso-butanol |

EXAMPLE 3

Dermatological/Cosmetic Preparation a) A 5% w/w dioctyl ester sodium sulfosuccinate (AEROSOL OT) in ethanol was prepared to obtain a wetting solution.
b) 10 g of zinc oxide was mixed with 50 ml of the wetting solution to obtain a dispersion.
c) The dispersion was mixed with a solution of 10 g of cetyl alcohol in 50 ml of chloromethane to obtain an oily suspension.
d&e) 0.35 g of sodium lauryl sulfate and 1.0 g of hexadecane were dissolved in 300 g deionized water at a temperature of 60° C. and stirred for 40 minutes, followed by cooling to room temperature to obtain an aqueous solution.

The remaining process steps were performed as described in Example 1.

Table II shows typical preparations useful in dermatology wherein ingredients from the columns are combined according to the process described in Example 1.

TABLE II

Dermatological/Cosmetic Preparations

| 0.01 to 5% w/w of Wetting Agent selected from the group | 2 to 18% w/w of Oily Substance selected from the group | 0.1 to 2% w/w of Emulsifying Agent selected from the group | 2 to 18% w/w of Particulate selected from the group | 20–80 ml of Organic Solvent selected from the group |
|---|---|---|---|---|
| Alkyl-benzene-sulfonate, Dioctyl ester sodium sulfosuccinate (AEROSOL OT), Sodium alkylaryl sulfonate (AEROSOL OS), Diethyl sulfosuccinate (AEROSOL MA), Sodium-2-ethylarylsulfate (TERGITOL 08), Sodium-3,9-diethyltridecyl-6-sulfate (TERGITOL 07), Sodium-7-ethyl-2-methyl-undecyl-4-sulfate (TERGITOL 04) Lanolin triethanolamine stearate | Cetyl alcohol, Olive oil, Cottonseed oil, Sesame oil, Glycerides, Liquid paraffin, Petroleum wax, Polyglycol esters | Sodium lauryl sulfate, Sodium dodecyl sulfate, Hexodecane, Cetyl alcohol, Stearyl alcohol | Zinc oxide, Starch containing an antiseptic therein, Talc, Calamine, Titanium dioxide, Magnesium carbonate | Chloromethane, Dichloromethane, Chloroform, Carbon tetrachloride Butanol Propanol Iso-propanol Iso-butanol |

Preparations of the present invention may include other ingredients commonly used in emulsions. For example, the dermatological formulations may include topical drugs for the treatment of diseases. Both the dermatological and cosmetic preparations ordinarily include preservatives against microbial growth examples of which include methyl, ethyl, propyl, and butyl parabens.

Penetration enhancers may also be included in the dermatological formulations, such as propylene glycol, glycerin, tetrahydrofurfunyl alcohol, dimethylacetamide, dimethylformamide, pyrrolidones, alkyl sulfoxides, phosphine oxides and sugar esters.

Stability studies at room and higher temperature were conducted to ascertain shelf-life of the emulsions of the present invention. At room temperature the emulsions remained homogeneous for at least four months, while at higher than room temperature, such as at 40°–50° C., they remained homogeneous for about 30 to 40 days. Upon vigorous agitation the emulsions, both at room and at higher temperatur, regained their initial homogenity and were then ready for their intended end use.

The invention, having been fully described, it will be apparent to one skilled in the art that changes and modifications can be made thereto without departing from the spirit and scope thereof.

What is claimed is:

1. A process for preparing an emulsion comprising the steps of:

a) preparing a solution of from about 0.01 to 5% w/w of a wetting agent selected from the group consisting of alkyl benzene sulfonate, sodium lauryl sulfate, sodium dilauryl phosphate, lanolin, sodium monoglyceryl lauryl sulfate, sodium methyl oleoyl taurate, sodium octoxynol-2-ethanesulfonate, di-β-naphthylmethane disulfate, sulfated castor oil, sodium secondary alcohol sulfate, sodium alkylaryl sulfonate, dialkylsulfosuccinate, dioctyl ester of sodium sulfosuccinate, sodium-7-ethyl-2-methyl-undecyl-4-sulfate, and sodium-3,9-diethyltridecyl-6-sulfate, in an organic solvent selected from the group consisting of ethyl alcohol, methyl alcohol, isopropyl alcohol, chloromethane, dichloromethane, chloroform, carbon tetrachloride, methyl ethyl ketone, methyl isobutyl ketone, ethyl acetate, perchloroethylene, acetone and glycol ethers to obtain a wetting solution;

b) mixing of 1 to about 90% w/w of a finely divided powder having 50 to 100 nm particle size distribution or less with the wetting solution to obtain a dispersion;

c) mixing the dispersion with from about 10 to about 99% w/w of an oily or polymeric substance dissolved in an organic solvent selected from the group consisting of ethyl alcohol, methyl alcohol, isopropyl alcohol, chloromethane, dichloromethane, chloroform, carbon tetrachloride, methyl ethyl ketone, methyl isobutyl ketone, ethyl acetate, perchloroethylene, acetone and glycol ethers to obtain an oily suspension;

d) preparing an aqueous solution by mixing in water of from about 0.1 to about 2% w/w of an emulsifying agent selected from the group consisting of a cationic, nonionic, anionic and zwitterionic surface active agent to obtain an aqueous solution;

e) adding of from about 20 to about 35% w/w of the oily suspension to about 65 to 80% w/w of the aqueous solution to obtain an aqueous suspension; and f) emulsifying the aqueous suspension.

2. The process of claim 1 further comprising removing said organic solvent from said aqueous suspension.

3. The process of claim 1 wherein said finely divided powder is selected from the group consisting of inorganic, organic and polymeric particles.

4. The process of claim 1 wherein said finely divided powder is selected from the group consisting of zinc oxide, titanium dioxide, talc, aluminum hydroxide, aluminum chloride, calcium phosphate, magnesium oxide, aluminum silicate, starch, calcium carbonate, magnesium carbonate, natural rubber, synthetic rubber, cellulose, polyamide resin and polyolefin resin.

5. The process of claim 1 wherein said emulsifying agent is selected from the group consisting of: potassium laurate, sodium dodecyl sulfate, ammonium lauryl sulfate, magnesium lauryl sulfate, triethanolamine lauryl sulfate, sulfated castor oil, dialkylglycerylphosphorylcholine, sodium lauryl sulfoacetate, sodium dodecyl benzenesulfonate, polyoxyethylated lauryl, hexadecyltrimethylammonium bromide or chloride, ethosylated para-octylphenol, 2-ethyl-hexyl alcohol ethoxylate and cetyltrimethyl ammonium persulfate.

6. The process of claim 1 wherein said oily or polymeric substance is selected from the group consisting of cetyl alcohol, lauryl alcohol, stearyl alcohol, olive oil, corn oil, tallow, shellac, lanolin, beeswax, polyurethane, phenolic resin, epoxide resin, nitrocellulose, acrylic polymer and styrene polymer.

7. A process of making an emulsion comprising the steps of:
  a) preparing a solution of from about 0.01 to 5% w/w of a wetting agent selected from the group consisting of alkyl benzene sulfonate, sodium lauryl sulfate, sodium dilauryl phosphate, lanolin, sodium monoglyceryl lauryl sulfate, sodium methyl oleoyl taurate, sodium octoxynol-2-ethanesulfonate, di-$\beta$-naphthylmethane disulfate, sulfated castor oil, sodium secondary alcohol sulfate, sodium alkylaryl sulfonate, dialkylsulfosuccinate, dioctyl ester of sodium sulfosuccinate, sodium-7-ethyl-2-methyl-undecyl-4-sulfate, and sodium-3,9-diethyltridecyl-6-sulfate, in an organic solvent selected from the group consisting of ethyl alcohol, methyl alcohol, isopropyl alcohol, chloromethane, dichloromethane, chloroform, carbon tetrachloride, methyl ethyl ketone, methyl isobutyl ketone, ethyl acetate, perchloroethylene, acetone and glycol ethers to obtain a wetting solution;
  b) mixing of 1 to 90% w/w of a finely divided powder having 50 to 100 nm particle size distribution with the wetting solution to obtain a dispersion;
  c) mixing the dispersion with of from about 10 to about 99% w/w of an oily or polymeric substance dissolved in an organic solvent selected from the group consisting of ethyl alcohol, methyl alcohol, isopropyl alcohol, chloromethane, dichloromethane, chloroform, carbon tetrachloride, methyl ethyl ketone, methyl isobutyl ketone, ethyl acetate, perchloroethylene, acetone and glycol ethers to obtain an oily emulsion;
  d) preparing an aqueous solution by mixing of from about 0.1 to about 2% w/w of an emulsifying agent selected from the group consisting of: potassium laurate, sodium dodecyl sulfate, ammonium lauryl sulfate, magnesium lauryl sulfate, triethanolamine lauryl sulfate, sulfated castor oil, dialkylglycerylphosphorylcholine, sodium lauryl sulfoacetate, sodium dodecyl benzenesulfonate, polyoxyethylated lauryl, hexadecyltrimethyl-ammonium bromide or chloride, ethoxylated para-octylphenol, 2-ethyl-hexyl alcohol ethoxylate and cetyltrimethyl ammonium persulfate, and from about 0.1 to about 6% of a co-surfactant selected from the group consisting of: lauryl-, cetyl-, myristyl, stearyl-, oleyl- and isocetyl-alcohols, lanolin, hexadecane, 1-pentanol, hexanol and decane by stirring for about 30 to 90 minutes at a temperature of from about 60° C. to about 70° C. to obtain an aqueous solution;
  e) cooling the aqueous solution to room temperature;
  f) adding from about 20 to about 35% w/w of the oily suspension to from about 65 to about 80% w/w of the aqueous solution and mixing them for about 20 to 30 minutes at room temperature to obtain an aqueous suspension;
  g) emulsifying the aqueous suspension by using an emulsifying technique to obtain an emulsion which contains organic solvents used in steps (a and c); and
  h) removing the organic solvent to obtain a final emulsion essentially free of the organic solvent.

* * * * *